(12) United States Patent
Wan et al.

(10) Patent No.: US 6,995,246 B1
(45) Date of Patent: Feb. 7, 2006

(54) METHODS FOR REMOVING SUSPENDED PARTICLES FROM SOLUBLE PROTEIN SOLUTIONS

(75) Inventors: Min Wan, Cary, NC (US); Susan M Rabideau, Garner, NC (US)

(73) Assignee: Akzo Nobel N.V., Arnhem (NL)

( * ) Notice: Subject to any disclaimer, the term of this patent is extended or adjusted under 35 U.S.C. 154(b) by 167 days.

(21) Appl. No.: 09/792,789

(22) Filed: Feb. 22, 2001

Related U.S. Application Data

(60) Provisional application No. 60/241,967, filed on Oct. 19, 2000.

(51) Int. Cl.
*C07K 1/14* (2006.01)

(52) U.S. Cl. ............... 530/412; 530/415; 530/427; 530/350; 502/412; 435/71.1; 435/91.1

(58) Field of Classification Search ............... 530/412, 530/415, 427, 350; 502/412; 435/71.1, 91.1; 514/2
See application file for complete search history.

(56) References Cited

U.S. PATENT DOCUMENTS

| | | | | |
|---|---|---|---|---|
| 3,852,496 A | * | 12/1974 | Weetall et al. | 426/41 |
| 3,984,539 A | * | 10/1976 | Khouw et al. | 424/169.1 |
| 4,000,121 A | * | 12/1976 | Garcia | 530/387.1 |
| 4,460,689 A | * | 7/1984 | Foor | 435/172 |
| 5,518,917 A | * | 5/1996 | Boyer et al. | 435/252.5 |
| 5,561,064 A | * | 10/1996 | Marquet et al. | 435/320.1 |
| 5,656,568 A | * | 8/1997 | Shiuh | 502/412 |
| 5,747,663 A | * | 5/1998 | Colpan et al. | 536/25.4 |
| 5,917,022 A | * | 6/1999 | Davies | 530/390.1 |
| 6,008,328 A | * | 12/1999 | Hsu et al. | 530/412 |
| 6,162,904 A | * | 12/2000 | Mamidi et al. | 530/390.1 |
| 6,197,571 B1 | * | 3/2001 | Hikichi et al. | 435/254.1 |
| 6,274,371 B1 | * | 8/2001 | Colpan | 435/259 |
| 6,313,285 B1 | * | 11/2001 | Butler et al. | 536/25.4 |
| 6,365,147 B1 | * | 4/2002 | Luo et al. | 424/93.1 |
| 6,468,534 B1 | * | 10/2002 | Hennen et al. | 424/157.1 |
| 6,504,012 B2 | * | 1/2003 | Mamidi et al. | 530/386 |
| 2001/0044136 A1 | * | 11/2001 | Lander | 435/91.1 |
| 2001/0053366 A1 | * | 12/2001 | Mapleson et al. | 424/204.1 |

OTHER PUBLICATIONS

Theodossiou, I., Bioprocess Engineering 16(3), 175–183, 1997.*
Petsch, D., Journal of Biotechnology 76(2,3), 97–119, 2000.*
Liu S., Clinical Biochemistry 30 (6) 455–63, 1997.*
Sharma, Satish K., Biotechnology and Applied Biochemistry 8(1), 5–22, 1986.*

* cited by examiner

*Primary Examiner*—Christopher S. F. Low
*Assistant Examiner*—David Lukton
(74) *Attorney, Agent, or Firm*—William P. Ramey

(57) ABSTRACT

The present invention provides soluble protein solutions, free of suspended particles in high yield. More particularly, the current invention provides a method for removing suspended particles from soluble protein solutions by filtering the soluble protein solution through highly purified diatomaceous earth.

8 Claims, 1 Drawing Sheet

AMINO ACID SEQUENCE OF SY161

|  |  |
|---|---|
| 1 | 20 |
| Ser Ser Cys Phe Asp Lys Gly Lys Tyr Lys Lys Gly Asp Asp Ala Ser Tyr Phe Glu Pro |  |
| 21 | 40 |
| Thr Gly Pro Tyr Leu Met Val Asn Val Thr Gly Val Asp Ser Ala Gly Asn Glu Leu Leu |  |
| 41 | 60 |
| Ser Pro His Tyr Val Glu Phe Pro Ile Lys Pro Gly Thr Thr Leu Thr Lys Glu Lys Ile |  |
| 61 | 80 |
| Glu Tyr Tyr Val Gln Trp Ala Leu Asp Ala Thr Ala Tyr Arg Glu Phe Arg Val Val Ala |  |
| 81 | 100 |
| Leu Ala Pro Ser Ala Lys Ile Ile Glu Val Ala Tyr Tyr Asp Lys Asn Lys Lys Asp Glu |  |
| 101 | 120 |
| Ser Lys Ser Phe Pro Ile Thr Ala Ala Gly Phe Val Val Pro Asp Leu Ser Glu His Ile |  |
| 121 | 136 |
| Lys Asn Pro Gly Phe Asn Leu Ile Thr Thr Val Val Ile Glu Arg Lys |  |

Figure 1

# METHODS FOR REMOVING SUSPENDED PARTICLES FROM SOLUBLE PROTEIN SOLUTIONS

This application claims the benefit under 35 U.S.C. § 119(e) of U.S. Provisional Application No. 60/241,967, filed Oct. 19, 2000, which is incorporated herein by reference in its entirety.

1. FIELD OF THE INVENTION

The present invention relates to methods for removing suspended particles from soluble protein solutions. In particular, the methods of the invention are useful for removing suspended particles from secreted protein solutions and lysates, including bacterial lysates containing a heterologous protein.

2. BACKGROUND OF THE INVENTION

Proteins play critical roles in functions such as metabolism, gene expression, signal transduction, cellular and extracellular structures, which are essential to the survival and/or reproduction of any living organism. Many proteins may be used in therapeutic and/or diagnostic applications, particularly when available in pure form. Contaminants often prevent realization of therapeutic and/or diagnostic goals and may endanger the health of a patient.

Protein purification is often a significant challenge, especially when large amounts of protein are required for therapeutic or diagnostic purposes. Procedures that simply and rapidly provide the protein of interest in pure form and high yield are very desirable, regardless of scale.

Removing suspended particles from soluble protein solutions is often an important practical problem in purifying proteins of therapeutic or diagnostic significance, particularly when heterologous proteins are expressed in either eukaryotic or procaryotic cells. Currently, several methods are used for removing suspended particles from soluble protein solutions.

Centrifugation is a common method for removing suspended particles from soluble protein solutions. In some situations, suspended particles may be removed from soluble protein solutions by centrifugation alone. In other instances, prior to centrifugation, soluble protein solutions, particularly bacterial lysates, may be treated with a flocculating agent (e.g., polyethyleneimine ("PEI")) which typically removes macromolecules (e.g., DNA and endotoxins) and cell debris. However, large scale centrifugation equipment is very expensive capital equipment and is often a limiting factor in removing suspended particles from soluble protein solutions on a process scale. Major problems with centrifugation include low yields and air entrapment in the supernatant that can lead to substantial protein denaturation. Typical yields of protein after centrifugation are about 80%–85%.

Aqueous two-phase partitioning is another method that has been used for removing cellular debris and suspended particles from soluble protein solutions. Liquid-liquid extraction relies on the incompatibility between two polymers in aqueous solution or one polymer and a salt present at high concentration. This incompatibility typically results in the formation of two separate phases of very different compositions. The protein molecules partition preferentially into one phase or the other, depending on their characteristics (Hayenga et al., U.S. patent application Ser. No. 09/307,549; Diamond et al., *Advances in Biochem. Eng. Biotechn.* 1992, 47:89–135).

However, aqueous two-phase extraction is time consuming, expensive and requires large amounts of chemicals, which must be properly disposed in compliance with environmental regulations. Further, the chemicals used in extraction must be removed from the protein of interest and the two-phase distribution of protein may limit product yield. Finally, two-phase extraction lacks generality since only a limited number of proteins can be purified by this method.

Microfiltration is another popular method for removing suspended particles from soluble protein solutions. Microfiltration uses membranes that either entrap particles on the membrane surface or within a bed of fibers found within the membrane. However, microfiltration on a process scale is a complicated operation that requires precise optimization of a number of variables such as transmembrane pressure, shear force, flow rate, concentration, pH, ionic strength, etc. Thus, process scale microfiltration frequently requires considerable development time.

Accordingly, what is needed is a rapid and inexpensive process that removes suspended particles from soluble protein solutions in high yield, particularly on a process scale. Further, such a process should not require the use of expensive capital equipment or large amounts of chemicals that require costly disposal.

3. SUMMARY OF THE INVENTION

The present invention addresses this need by providing rapid, efficient and inexpensive methods for removing suspended particles from soluble protein solutions. The present invention provides soluble protein solutions, free of suspended particles in high yield, while avoiding the use of expensive capital equipment or chemicals that require expensive disposal.

The current invention provides a method for removing suspended particles from soluble protein solutions by filtering the soluble protein solution through highly purified diatomaceous earth. Preferably, the highly purified diatomaceous earth is Celpure™ P-1000.

In one embodiment, the soluble protein solution is a secreted protein solution. In another embodiment, the soluble protein solution is a lysate. In a preferred embodiment, the lysate is a bacterial lysate.

Preferably, the amount of DNA and endotoxins in a bacterial lysate is reduced. Then, the lysate is filtered through highly purified diatomaceous earth to remove suspended particles, which dramatically reduces lysate turbidity. In one embodiment, the highly purified diatomaceous earth is packed in a filter press.

In a preferred embodiment, flocculation with polyethyleneimine at between about pH 7.3 and about pH 7.7 reduces the amount of DNA and endotoxins in the lysate. Preferably, the amount of DNA in the lysate is reduced by between about 100-fold and about 150-fold. In one embodiment, the amount of endotoxins in the lysate is reduced by between about 1,000-fold and about 10,000-fold. In another embodiment, the turbidity of the lysate is reduced by between about 200-fold and about 300-fold.

In another preferred embodiment, the lysate is filtered through highly purified diatomaceous earth with a filter press. In a more specific embodiment, the lysate is stirred with highly purified diatomaceous earth before filtering through the filter press. Preferably, the yield of the soluble protein solution is between about 95% and about 100% after filtration through highly purified diatomaceous earth.

In yet another preferred embodiment, the lysate is a bacterial lysate containing a heterologous protein that was obtained by expression in bacteria Preferably, the heterologous protein is SY161, which has the amino acid sequence shown in SEQ. ID. NO. 1. In a more specific embodiment, refractile bodies in the lysate are resolubilized. Preferably, the bacteria is *E. coli.*

In one embodiment, the cysteine residues of the heterologous protein are blocked. Preferably, the cysteine residues are blocked with an oxidizing agent. More preferably, the oxidizing agent is a mixture of sodium sulfite and sodium tetrathionate. Even more preferably, about a 2:1 ratio of sodium sulfite and sodium tetrathionate are added to the heterologous protein at a pH of between about 7.8 and about 8.2.

In another embodiment, the blocked cysteine residues of the heterologous protein are deblocked. Preferably, a reducing agent is used to deblock the heterologous protein. More preferably, the reducing agent is dithiothreitol.

4. BRIEF DESCRIPTION OF THE DRAWINGS

FIG. 1 provides the amino acid sequence (SEQ ID NO 1) of SY161.

5. DETAILED DESCRIPTION OF THE INVENTION

The present invention relates to methods for removing suspended particles from soluble protein solutions. The details for practicing the invention are described in the subsections below.

5.1 Sources of Soluble Protein Solutions

Soluble protein solutions may be prepared by any art-known technique. Thus, for example, soluble protein solutions may be obtained by culturing procaryotes that secrete either wild-type or heterologous proteins, lysis of procaryotes, lysis of procaryotes that express heterologous proteins, lysis of eucaryotes, lysis of eucaryotes expressing heterologous proteins, growing eucaryotes that secrete a soluble protein, dissolving commercially available proteins in solution, etc.

Procaryotes can provide soluble protein solutions after cell lysis. Alternatively, microorganisms that secrete either wild type or heterologous proteins may be cultured to provide soluble protein solutions. Wild-type prokaryotic cells or those expressing heterologous proteins, can be grown under a variety of conditions known to the skilled artisan. Methods of growing inocula and inoculating culturing medium are known to the skilled artisan and exemplary methods have been described in the art. Preferred media, times, temperatures and pH for culturing microorganisms are also known in the art. Thus, for example, the cells are grown in a medium suitable for growth of such cells, for example, minimal media or complete (i.e., rich) media.

Soluble protein solutions containing a heterologous protein may be advantageously produced by recombinant DNA technology using techniques well known in the art for expressing genes. These methods include, for example, in vitro recombinant DNA techniques, synthetic techniques, and in vivo genetic recombination. See, for example, the techniques described in Sambrook et al., "Molecular Cloning," Cold Spring Harbor Laboratory Press, Cold Spring Harbor, N.Y., Vols. 1–3:(1989), and periodic updates thereof, and Ausubel et al., eds., 1989, "Current Protocols in Molecular Biology," Green Publishing Associates, Inc., and John Wiley & Sons, Inc., New York. DNA and RNA encoding any heterologous protein may be chemically synthesized using, for example, synthesizers. See, for example, the techniques described in "Oligonucleotide Synthesis", 1984, Gait, M. J. ed., GIRL Press, Oxford.

A variety of host-expression vector systems may be utilized to express proteins. The expression systems that may be used for purposes of the invention are microorganisms such as bacteria (e.g., *E. coli, B. subtilis*) transformed with recombinant bacteriophage DNA, phasmid DNA or cosmic DNA expression vectors containing a nucleotide sequence encoding the desired protein; yeast (e.g., Saccharomyces, Pichia) transfected with recombinant yeast expression vectors containing a nucleotide sequence encoding the protein of interest; insect cell systems infected with recombinant virus expression vectors (e.g., baculovirus) containing a nucleotide sequence encoding the protein of interest; plant cell systems infected with recombinant virus expression vectors (e.g., cauliflower mosaic virus, CaMV; tobacco mosaic virus, TMV) or transfected with recombinant plasmid expression vectors (e.g., Ti plasmid) containing a nucleotide sequence encoding the protein of interest; or mammalian cell systems (e.g., COS, CHO, BHK, 293, 3T3, U937) harboring recombinant expression constructs containing promoters derived from the genome of mammalian cells (e.g., metallothionein promoter) or from mammalian viruses (e.g., the adenovirus late promoter, the vaccinia virus 7.5K promoter).

In eukaryotic systems, a number of selection systems may be used, such as for example, the herpes simplex virus thymidine kidnase (Wigler et al., 1977, *Cell*, 11, 223), hypoxanthine-guanine phosphoribosyltransferase (Szybalska et al., 1962, *Proc. Natl. Acad. Sci.*, USA 48, 2026), and adenine phosphoribosyltransferase (Lowy et al., 1980, *Cell*, 22, 817) genes can be employed in tk⁻, hprt⁻ or aprt⁻ cells, respectively. Also, antimetabolite resistance can be used as the basis of selection for the following genes: dhfr, which confers resistance to methotrexate (Wigler et al., 1980, *Proc. Natl. Acad. Sci.*, USA 77, 3567; O'Hare et al., 1981, *Proc. Natl. Acad. Sci.*, USA 78, 1527); gpt, which confers resistance to mycophenolic acid (Mulligan et al., 1981, *Proc. Natl. Acad. Sci.* USA 78, 2072); neo, which confers resistance to the aminoglycoside G-418 (Colberre-Garipin et al., 1981, *J. Mol. Biol.* 150, 1); and hygro, which confers resistance to hygromycin (Santerre et al., 1984, Gene, 30, 147).

In bacterial systems, as previously mentioned, a number of expression vectors may be selected. Bacteria suitable for the practice of the invention are gram positive and gram negative bacteria. In a preferred embodiment, soluble protein solutions are obtained by expression of heterologous proteins in *Eschericia coli* ("*E. coli*") and subsequent cell lysis.

The protein can be expressed in a procaryotic cell using expression systems known to those of skill in the art of biotechnology. Expression systems useful for the practice of the current invention are described in U.S. Patent Nos. 5,795,745; 5,714,346; 5,637,495; 5,496,713; 5,334,531; 4,634,677; 4,604,359; 4,601,980, all of which are incorporated herein by reference in their entirety.

Procaryotic cells can be grown under a variety of conditions known to the skilled artisan. In one aspect of the current invention, the cells are grown in a medium suitable for growth of such cells, for example, minimal media or complete (i.e., rich) media Staphylokinase is a potent, uniquely fibrin-selective thrombolytic agent that has substantial therapeutic value in the treatment of acute myocardial infarction and ischemic stroke (Collen, *Nature Medicine*, 1998, 279). The staphylokinase gene has been cloned from a variety of sources including a *Staphylococcus aureus* strain and has been expressed in *E. coli* (Sako et al., *Mol. Gen. Genet.*, 1983, 271; Behnke et al., *Mol. Gen. Genet.*, 1987, 528; Colleen et al., *Fibrinolysis* 6, 203). A number of natural variants of the staphylokinase gene from *Staphylococcus aureus* have been isolated (Kim et al., *Thrombosis Research*, 1997,387).

SY161 is a staphylokinase analogue that differs at thirteen amino acids from the amino acid sequence of the native protein, while retaining significant in vivo thrombolytic activity (Collen et al., *Circulation* 102, 1766,2000). A modification of SY161 (i.e., attachment of polyethylene glycol to the lone cysteine in the protein) that increases half-life and decreases immunogenicity is currently in clinical trials for treatment of myocardial infarction and peripheral arterial occlusion. A preferred soluble protein solution that may be used in practicing the current invention may be obtained by lysis of *E. coli* strains that express SY161.

5.2. Removing Suspended Particles From Soluble Protein Solutions

The current invention removes suspended particles from soluble protein solutions. Soluble protein solutions may be obtained from cells, cell homogenates, disrupted cells, etc. and can be prepared in a variety of ways. For example, a paste of frozen dead cells may be prepared, living cells may be frozen or living cells may be used directly in the method of the current invention.

The method of the current invention relates to filtering suspended particles from soluble protein solutions. Suspended particles are frequently formed when cells are lysed and may include insoluble precipitates along with cell debris. Further, suspended particles are often found in solutions of soluble proteins secreted either by microorganisms or eucaryotes. Suspended particles are often difficult to remove from soluble protein solutions because of their small size.

In one embodiment, suspended particles are removed from a soluble protein solution obtained by secretion. In another embodiment, suspended particles are removed from a soluble protein solution obtained by cell lysis.

In a preferred embodiment, bacterial cells are lysed to form soluble protein solutions. In a specific embodiment, *E. coli* cells that express a heterologous protein, such as SY161, are lysed. In another embodiment, *E. coli* cells that express wild type protein are lysed.

A number of methods well-known in the art may be used to lyse bacterial cells such as bead mills, osmotic shock, freeze fracture and enzymatic treatment. Preferably, a high pressure homogenizer, such as a microfluidizer, is used to lyse bacterial cells.

Lysis of bacterial cells releases substantial amounts of DNA and endotoxins into the lysate. Preferably, the amount of DNA and endotoxins in the bacterial lysate are reduced prior to removing suspended particles. Many methods for removing DNA and endotoxins from bacterial lysates are known to those of skill in the art. These methods, include but are not limited to, ammonium sulfate precipitation, anion exchange chromatography or filtration.

In a preferred embodiment, DNA and endotoxins in a bacterial lysate are reduced by flocculation. Preferably, flocculation is performed with polyethyleneimine at between about pH 7.3 and about pH 7.7. Other flocculation methods are known to those of skill in the art. Typically, flocculation reduces the amount of DNA in the lysate by between about 100-fold to about 150-fold and the amount of endotoxins by between about 1,000-fold and about 10,000-fold, as measured by conventional DNA threshold methods and Limulus Amoebocyte Lysate (LAL) methods, respectively.

Flocculant and suspended particles are then removed from lysate by filtration through highly purified diatomaceous earth. Diatomaceous earth (i.e., kieselguhr), is a light colored, porous sedimentary rock composed of the silaceous shells of diatoms, which are unicellar aquatic plants of microscopic size. When well hardened, diatomaceous earth is commonly called diatomite.

Diatomaceous earth has been used in a number of different situations, including but not limited to, separation, adsorption, support and functional filler applications (Breese, (1994) "*Industrial Minerals and Rocks*," $6^{th}$ ed., Littleton, Colo.: Society for Mining, Metallurgy and Exploration, pp. 397–412). Diatomaceous earth is known in the art as a filtration aid and has been used, for example, in the processing of oils, beverages, solvents and chemicals on an industrial scale.

Diatomaceous earth may be obtained in a variety of different grades and purity. A significant problem with the use of diatomaceous earth typically available from commercial suppliers, in biological applications, is leaching of significant amounts of impurities from the diatomaceous earth into biological solutions.

Preferably, highly purified diatomaceous earth is used to practice the current invention Methods for preparing highly purified diatomaceous earth have been described in the art (Shiuh et al., U.S. Pat. No. 5,656,568, which is herein incorporated by reference). Preferably, Celpure™ (most preferably, Celpure™ P-1000) a grade of highly purified diatomaceous earth is used to practice the current invention (Advanced Minerals, Inc., 130 Castilian Drive, Santa Barbara, Calif., 93117).

Highly purified diatomaceous earth such as Celpure™ has the following general characteristics: extremely high purity, low density, low soluble impurity content, low total impurity content, and high brightness (Shiuh et al., U.S. Pat. No. 5,656,568). The highly purified diatomaceous earth (i.e., Celpure™) used to practice the invention should have been leached in appropriate media (e.g., by acid treatment) to remove soluble impurities, have a total $SiO_2$ content of at least about 95% and a silica specific volume of greater than about 3.4 (Shiuh et al., U.S. Pat. No. 5,656,568).

The bead size of the highly purified diatomaceous earth used to practice the current invention is typically determined by the volume of the soluble protein solution. While small bead sizes may provide reasonable protein recovery, the amount of back pressure generated is unacceptable when large volumes of soluble protein are filtered. Generally, larger beads provide a better filter cake and lower back pressure and are preferred for at least these 25 reasons.

Preferably, the lysate is stirred with highly purified diatomaceous earth before filtration through a filter press. Typically, the yield of soluble protein solution after filtration through highly purified diatomaceous earth is between about 95% and about 100%, as measured by quantitative reverse phase HPLC.

In some situations, protection of cysteine residues in the soluble protein solution (preferably, a bacterial lysate containing a heterologous protein expressed in bacteria) may be desirable. Cysteine protection may prevent protein intermolecular or intramolecular disulfide bond formation and/or undesirable sulfhydryl oxidation. Preferably, the soluble protein solution is treated with a sulfhydryl protecting group, which may be selected from the many reagents that have been described in the art (see e.g., Greene et al., "Protective Groups in Organic Synthesis", Chapter 6, John Wiley & Sons). Appropriate sulfhydryl protecting groups include, but are not limited to, disulfides, sulfenyl compounds, thiocarbamates, thiocarbonates, thioesters, thioethers, etc.

In an exemplary embodiment, the sulfhydryl groups of cysteine residues of the soluble protein solution preferrbly, a bacterial lysate containing a heterologous protein) are blocked by oxidation to a disulfide or sulfenyl group. Preferably, sulfonation with sodium sulfate and sodium tetrathionate is used to block the sulfhydryl groups. Other methods for forming sulfonates are known to the skilled artisan. Ideally, about a 2:1 ratio of sodium sulfite and sodium tetrathionate are added to the soluble protein solution, which is adjusted to a pH of between about 7.8 and about 8.2. Preferably, when the soluble protein solution is a bacterial lysate containing a heterologous protein, the sulfhydryl groups of cysteine residues are protected after cell lysis and before flocculation.

The cysteine protecting group should also be readily removable. Many methods for converting disulfides, sulfenyl compounds, thiocarbamates, thiocarbonates, thioesters, thioethers, etc. to the free thiol have been described in the art (see e.g., Greene et al., "Protective Groups in Organic Synthesis", Chapter 6, John Wiley & Sons). In an exemplary embodiment, when the cysteine residues in the soluble protein solution have been protected by sulfonation, they are deblocked with a reducing agent. Many reducing agents are known in the art and include, but are not limited to, sodium borohydride, mercaptans (e.g., 2-mercaptoethanol, methythioglycoloate, 3-mercapto-1,2-propanediol, 3-mercaptoproprionic acid, dithioeyihritol and dithiothreitol), tri-n-butyl phosphine, hydrogen in the presence of noble metal catalysts and alkali in liquid ammonia. Preferably, dithiothreitol is used to deprotect the cysteine residues of the soluble protein solution when a sulfonate has been used as the protecting group. The cysteine protecting group may be removed after lysate flocculation (e.g., when the soluble protein solution is a bacterial lysate containing a heterologous protein) or any other subsequent purification step.

In some cases, substantial amounts of heterologous protein may be precipitated within the bacterial cell as retractile bodies. In this situation, cell lysis will provide a lysate that contains substantial amounts of refractile bodies. Preferably, these refractile bodies are resolubilized and the resulting heterologous protein restored to active form, prior to removing suspended particles from the lysate. Otherwise, large quantities of the heterologous protein will be removed during filtration, which greatly reduces the overall yield of the process. Methods for resolubilizing refractile bodies and restoring the resulting heterologous protein to active form are known to the skilled artisan (see, e.g., Jones et al., U.S. Pat. No. 4,512,922). Preferably, refractile bodies are resolubilized and restored to active form prior to lysate flocculation.

5.3 Processing of the Soluble Protein Solution Following Removal of Suspended Particles Soluble protein solutions may be further processed, for example, in order to provide a soluble protein solution of a higher level of purity. The level of purity required will depend on the potential use of the protein. For example, therapeutic uses will typically require extensive further purification following application of the method of the current invention.

Any protein purification methods known to the skilled artisan may be used for further purification. Such techniques have been extensively described in "New Protein Techniques: Methods in Molecular Biology," Walker, J. M., ed., Humana Press, Clifton, N.J., 1988; and Protein Purification: Principles and Practice, 3rd. Ed., Scopes, R. K., Springer-Verlag, New York, N.Y., 1987. In general, techniques including, but not limited to, ammonium sulfate precipitation, centrifugation, ion exchange chromatography, affinity chromatography, gel filtration, reverse-phase chromatography (and the HPLC or FPLC forms thereof), and adsorption chromatography may be used to further purify a soluble protein solution.

The following examples are provided to further illustrate the current invention but are not intended to limit the scope of the current invention in any way.

6. EXAMPLE 1

Removing Suspended Particles From *E. coli* Lysate Containing SY161

6.1. Lysis of *E. coli* Cells Expressing SY161

SY161 may be produced in *E. coli* strain TGI transformed with plasmid pMc5-SY161-S3C. This clone represents 13 mutations from the original Staphylokinase gene subcloned from *Staphylococcus aureus*.

The *E. coli* cells expressing SY161 were harvested by centrifugation and stored at −70° C. prior to use. The frozen cell paste was broken into pieces and suspended in about 7.0 volumes (weight/volume) of lysate buffer (50 mM sodium phosphate, pH 9.5 containing 5 mM EDTA) using an overhead mixer set at between about 500 RPM to about 1000 RPM. Mixing was continued until the cell paste was completely suspended in the lysate buffer. A microfluidizer unit was assembled by connecting the required air pressure lines, coolant lines and hoses. The microfluidizer was then purged with lysate buffer and the pressure was adjusted to between about 13,000 psi to about 14,000 psi. The suspended cell paste was transferred to a pressure vessel, which was then sealed and adjusted to a pressure of about 30 psi. A stainless steel in-line filter was then connected to the bottom of the pressure vessel to prevent large cell clumps from clogging the microfluidizer. A feed line was attached to the pressure vessel containing the suspended cell paste. The homogenizer was turned on, the feed valve was opened and the pressure of the system was allowed to equilibrate until it was between about 13,000 psi to about 14,000 psi. The once-lysed cell suspension was collected in a clean tank and the system was rinsed with appropriate quantities of lysate buffer. The above procedure was then repeated to provide a twice-lysed cell suspension containing SY161.

6.2. Lysate Sulfonation

The lysate prepared in Section 5.1 was stirred until well suspended. If necessary, the pH of the lysate was adjusted to about 8.0±0.2 with either dilute acid or base. The target lysate volume may be calculated by multiplying the weight of the cell paste used in the procedure above by 10. Lysate buffer was added with stirring until the desired volume was reached. The amount of sulfitolysis stock solution that was added to the lysate may be readily approximated by multiplying the lysate volume by 0.05 (the stock solution was a mixture of 200 mg/ml sodium sulfite and 100 mg/ml sodium tetrathionate). The appropriate amount of sulfitolysis stock solution was added to the lysate, which was mixed for about 4.0 hours at room temperature until sulfonation of SY161 was complete.

6.3 Lysate Flocculation

A 10% phosphoric acid was slowly added with mixing to the sulfonated lysate prepared in Section 5.2 until the lysate reached a pH of about 7.5±0.2. A 5% (w/w) polyethyleneimine ("PEI") stock solution was prepared by diluting 50% PEI to 5% and adjusting the pH to about 7.5±0.2 with hydrochloric acid. The volume of PEI stock solution used for flocculation may be estimated by dividing the volume of sulfonated lysate by 25. The appropriate amount of PEI stock solution was added to the lysate to provide a final PEI concentration of about 0.2%. The flow rate of PEI addition was a critical parameter and may be calculated by multiplying the volume of pH adjusted sulfonated lysate by 0.8, which provided an appropriate flow rate in milliliter per minute. If PEI was added at too rapid of a rate the product protein was co-flocculated, which significantly reduced the yield of the process. The calculated volume of 5% PEI was added to the sulfonated lysate at the flow rate calculated from the formula provided above. The sulfonated lysate was gently stirred during PEI addition, although vortexing or foaming was avoided.

6.4. Lysate Filtration

The amount of highly purified diatomaceous earth (e.g., Celpure™ P-1000) added to the lysate prepared in Section 5.3 may be estimated by multiplying the volume of the lysate in liters by 0.06, which provided a Celpure™ P-1000 concentration of about 6%. Table 1 provides the relationship among the bead size, percentage of activity and product recovery. Small beads such as Celpure™ P-65 provided reasonable recovery but generated higher back-pressure, which is unacceptable in large scale. Generally, larger beads provided a better filter cake and preferred for this reason. The calculated amount of Celpure™ P-1000 was added to the lysate with mixing. Importantly, mixing should be done at the lowest rate necessary to provide a suspension of Celpure™ P-1000.

TABLE 1

| Test | Activity (HU/Assay) | Recovery (%) |
| --- | --- | --- |
| Total Lysate (%) | 43.46 | 100 |
| 4% Celpure ™ P-65 | 37.51 | 86.31 |
| 6% Celpure ™ P-65 | 27.85 | 64.09 |
| 2% Celpure ™ P-300 | 36.74 | 84.54 |
| 4% Celpure ™ P-300 | 33.11 | 76.18 |
| 6% Celpure ™ P-300 | 40.62 | 93.47 |
| 4% Celpure ™ P-1000 | 35.48 | 81.63 |
| 6% Celpure ™ P-1000 | 48.52 | 111.65 |

The filter press was prepared as follows. Fresh filter pads (preferably, filter cloth septums from Nylon filter cloth S/46412-4-CHS made by Komline-Sanderson) were installed and a filter press (preferably, a Begerow BECO-ASF 4000 filter press) was rinsed and equilibrated. It should be noted that Nylon filter cloth was critical to filtration of the lysate through highly purified diatomaceous earth. The hold-up volume of the filter press may be estimated at this time. The amount of Celpure™ P-1000 pre-coat used in the filter press may be calculated by multiplying the filtration surface area, in square meters, by 1000 (each filter sheet is 0.14 m$^2$. The required amount of Celpure™ P-1000 was suspended in approximately 50 liters of filtration buffer (i.e., 50 mM sodium phosphate, pH 7.5) and the filter press was pre-coated by circulating the Celpure™ P-1000 suspension through the filter press until the suspension became clear. Lysate filtration commenced immediately at a flow rate of between about 5 and about 10 liters per minute. The filtrate and filter cake wash were collected and any liquid remaining in the filter press was removed by flushing with compressed air. The filter cake retained cell debris such as suspended particles and flocculated material. The turbidity of the lysate was reduced from about 1800 Nephelometric Turbidity Units ("NTU") to less than about 10 NTU. The yield of SY161 was between about 95% and about 100%. The clear solution was directly used in further applications.

7. EXAMPLE 2

Removing Suspended Particles From *E. coli* Lysate

7.1 Lysis of *E. coli* Cells that do not Express a Hetrologous Protein

*E. coli* null cells (*E. coli* TG1, pMc5–8 (Δ clone)) for expression of SY161 were harvested by centrifugation and stored at −70° C. prior to use. The frozen cell paste was suspended in about 7.0 volumes (weight/volume) of lysate buffer (50 mM sodium phosphate buffer, pH 9.5, containing 5 mM EDTA). The frozen cell paste was stirred for about 0.5 hour with a Silverson Lab Mixer Emulsifier (Model L4R) at about 3,000 rpm to resuspend the cells. A microfluidizer (Model 110Y) was connected to compressed air and the cooling chamber was filled with ice. The homogenizer was purged with lysate buffer and the pressure was adjusted to between about 13,000 psi to about 14,000 psi. The suspended cells were fed into a homogenizer and lysed under the operational pressure of between about 13,000 psi to about 14,000 psi. The once-lysed cell suspension was collected in a clean container and the system was rinsed with appropriate quantities of lysate buffer. The above procedure was then repeated to provide a twice-lysed cell suspension containing *E. coli* host cell proteins.

7.2 Lysate Flocculation

10% phosphoric acid was slowly added to the lysate prepared in Section 7.1 with mixing, until the lysate pH reached a pH of about 7.5±0.2. A 5% (w/w) PEI stock solution was prepared by diluting 50% PEI to 5% and adjusting the pH to 7.5±0.2 with hydrochloric acid. The appropriate amount of PEI stock solution was then added to provide a final PEI concentration of about 0.2%. The flow rate of PEI addition was calculated by multiplying the volume of the lysate by 0.8, which provided an appropriate flow rate in milliliter per minute. If PEI was added too rapidly, the *E. coli* proteins can be co-flocculated which would significantly reduce the yield of the process. The lysate was gently stirred during the PEI addition, although vortexing or foaming was avoided.

7.3 Lysate Filtration

The amount of highly purified diatomaceous earth (e.g., Celpure™ P-1000) added to the flocculated lysate was estimated by multiplying the volume of the flocculated lysate in liters by 0.09, which provides a Celpure™ P-1000 concentration of 9%. The calculated amount of Celpure™ P-1000 (about 450 g of Celpure™ P-1000 was added to about 5L of lysate) was added to the lysate with mixing.

A Komline-Sanderson Avery Filter Press, Model 177 Laboratory Filter Press and Nylon filter cloth were used in the filtration process. The system hold-up volume was about 1.8 L. The lysate-DE mixture was recycled by pumping the mixture through the filter press with a Sandpiper pump, (model PB ½-A) and maintaining the air pressure between about 25 psi and 40 psi until the filtrate was cleared. The filtrate was then directed with an outlet tube to a clean container. The hold-up liquid was removed by connecting the filter press to compressed air. An SDS-PAGE gel indicated that no protein species were lost during flocculation and filtration. However, most DNA and endotoxin were removed from the lysate.

The addition of PEI was critical for removing suspended particles from the soluble protein solution as shown in Table 2. Table 2 illustrates endotoxin removal and removal of suspended particles from lysate with and without PEI addition Removal of suspended particles in the lysate was conveniently monitored by turbidity measurements of the lysate using an HACH 2100 AN turbidimeter. Endotoxin removal was measured by LAL.

The turbidity reading of the lysate was 1875 NTU, while the amount of endotoxins was greater than about 3,000,000 EU/ml (see line 1, Table 2) prior to addition of PEI and filtration in Experiment 1. After filtration, the amount of endotoxins (i.e., 30 EU) and suspended particles (i.e., 7 NIU) were greatly reduced (compare line 1 to line 2, Table 2) in Experiment 1.

The turbidity reading of the lysate was 2625 NTU, while the amount of endotoxins were greater than about 3,000,000 EU/ml (see line 3, Table 3) prior to filtration in Experiment 2 (no PEI added). After filtration, the amount of endotoxins (i.e., 3,000,000 EU) and suspended particles (i.e., 130 NTU) were reduced (compare line 3 to line 4, Table 2) but were significantly greater than when PEI was added to the lysate in Experiment 1 (compare line 2 and line 4, Table 2). Thus, PEI addition may increase the removal of suspended particles by about 10-20-fold and reduce the amount of endotoxin in the filtrate by about 10,000-fold.

The present invention is not to be limited in scope by the exemplified embodiments which are intended as illustrations of single aspects of the invention and any sequences which are functionally equivalent are within the scope of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

TABLE 2

Comparison of an *E. coli* lysate after PEI addition and filtration with an *E. coli* lysate after filtration without PEI addition.

| Line | Exp | Sample | Dilution | Turbidity (NTU) Reading | Total NTU | Endotoxin Endotoxin Unit per ml (EU/ml) |
|---|---|---|---|---|---|---|
| 1 | 1 | Lysate | 15 | 125 | 1875 | >3,000,000 |
| 2 | 1 | Lysate after PEI addition and filtration | 1 | 7 | 7 | 30 |
| 3 | 2 | Lysate | 15 | 175 | 2625 | >3,000,000 |
| 4 | 2 | Lysate after filtration. | 1 | 130 | 130 | 3,000,000 |

What is claimed is:

1. A method for removing suspended particles from a soluble protein solution comprising the steps of:
   filtering the soluble protein solution through highly purified diatomaceous earth, thereby providing a clarified soluble protein solution; and,
   reducing the amount of DNA and endotoxins by flocculation with polyethylencimine at a pH of between about pH 7.3 and about pH 7.7.

2. A method for removing suspended particles from a soluble protein solution comprising the steps of:
   filtering the soluble protein solution through highly purified diatomaceous earth, thereby providing a clarified soluble protein solution; and,
   reducing the amount of DNA and endotoxins, wherein the protein solution is a lysate, and wherein the yield of the protein is between about 95% and about 100%.

3. A method for removing suspended particles from a soluble protein solution comprising the steps of
   filtering the soluble protein solution through highly purified diatomaceous earth, thereby providing a clarified soluble protein solution;
   reducing the amount of DNA and endotoxins, wherein the protein solution is a lysate, wherein the lysate is a bacterial lysate containing a heterologous protein that was obtained by expression; and,
   resolubilizing retractile bodies in the lysate.

4. A method for removing suspended particles from a soluble protein solution comprising the steps of
   filtering the soluble protein solution through highly purified diatomaceous earth, thereby providing a clarified soluble protein solution and
   reducing the amount of DNA and endotoxins, wherein the protein solution is a lysate, wherein the lysate is a bacterial lysate containing SY161, wherein SY161 has an amino acid sequence as shown in SEQ ID NO: 1.

5. The method of claim 1, 2, 3, or 4 wherein the protein comprises cysteine residues and those residues are protected by treating the residues with a protecting group selected from the group consisting of disulfides, sulfenyl compounds, thiocarbamates, thioesters, and thioethers.

6. The method of one of claim 1, 2, 3, or 4 wherein the protein comprises a cysteine residue and the residue is blocked by oxidation.

7. The method of claim 5 further comprising the step of removing the protecting group.

8. The method of claim 6 further comprising the step of deblocking the residue with a reducing agent.

* * * * *

SEQUENCE LISTING

```
<160> NUMBER OF SEQ ID NOS: 1

<210> SEQ ID NO 1
<211> LENGTH: 136
<212> TYPE: PRT
<213> ORGANISM: SY161

<400> SEQUENCE: 1

Ser Ser Cys Phe Asp Lys Gly Lys Tyr Lys Lys Gly Asp Asp Ala Ser
1               5                   10                  15

Tyr Phe Glu Pro Thr Gly Pro Tyr Leu Met Val Asn Val Thr Gly Val
            20                  25                  30

Asp Ser Ala Gly Asn Glu Leu Leu Ser Pro His Tyr Val Glu Phe Pro
        35                  40                  45

Ile Lys Pro Gly Thr Thr Leu Thr Lys Gly Lys Ile Glu Tyr Tyr Val
    50                  55                  60

Gln Trp Ala Leu Asp Ala Thr Ala Tyr Arg Glu Phe Arg Val Val Ala
65                  70                  75                  80

Leu Ala Pro Ser Ala Lys Ile Glu Val Ala Tyr Tyr Asp Lys Asn Lys
                85                  90                  95

Lys Lys Asp Glu Ser Lys Ser Phe Pro Ile Thr Ala Ala Gly Phe Val
```

```
                    100                 105                 110
Val Pro Asp Leu Ser Glu His Ile Lys Asn Pro Gly Phe Asn Leu Ile
        115                 120                 125

Thr Thr Val Val Ile Glu Arg Lys
    130                 135
```